United States Patent [19]
Phillips

[11] Patent Number: 5,556,761
[45] Date of Patent: Sep. 17, 1996

[54] TEST STRIP FOR BLOOD GLUCOSE TESTING

[76] Inventor: Kevin J. Phillips, 132 Main St., Chester, S.C. 29706

[21] Appl. No.: 233,376

[22] Filed: Apr. 26, 1994

[51] Int. Cl.⁶ .............................. G12Q 1/54; G01N 31/00; G01N 21/00
[52] U.S. Cl. .................... 435/14; 435/4; 435/970; 436/14; 422/55; 422/57; 422/82.05; 422/85; 422/87
[58] Field of Search ................. 435/14, 4, 970; 436/14; 422/55, 57, 82.05, 85, 87

[56] References Cited

U.S. PATENT DOCUMENTS

| | | | |
|---|---|---|---|
| 5,187,100 | 2/1993 | Matzinger et al. | 435/14 |
| 5,212,060 | 5/1993 | Maddox | 435/14 |
| 5,306,623 | 4/1994 | Kiser et al. | 435/14 |

OTHER PUBLICATIONS

Hitadii Chemical, *Derwent Abstract*, Accession Numbers 84–192252/31 and 84–109197 (JP. No. 59–109197, Jun. 23, 1984).

Konisiroku Photo Industry Co. Ltd., *Chemical Abstracts*, vol. 97, p. 450 Ref. #178368s, 1982.

Ionescu, *Chemical Abstracts*, vol. 92, p. 308, Ref. #72300v, 1980.

*Primary Examiner*—Elizabeth C. Weimar
*Assistant Examiner*—Abdel A. Mohamed
*Attorney, Agent, or Firm*—B. Craig Killough

[57] ABSTRACT

A test strip for determining blood glucose levels comprising a reagent which incorporates a dye color. Whole blood reacts with the reagent of the test strip resulting in a color change on the reagent portion of the strip which is controlled by the dye color, indicating the blood glucose level by visual comparison with a color chart, or by the use a photometer. The use of a copolymer in the reagent which provides complete coalescence and a resulting smooth surface particle structure provides accurate readings of the reacted test strip by the photometer.

19 Claims, 1 Drawing Sheet

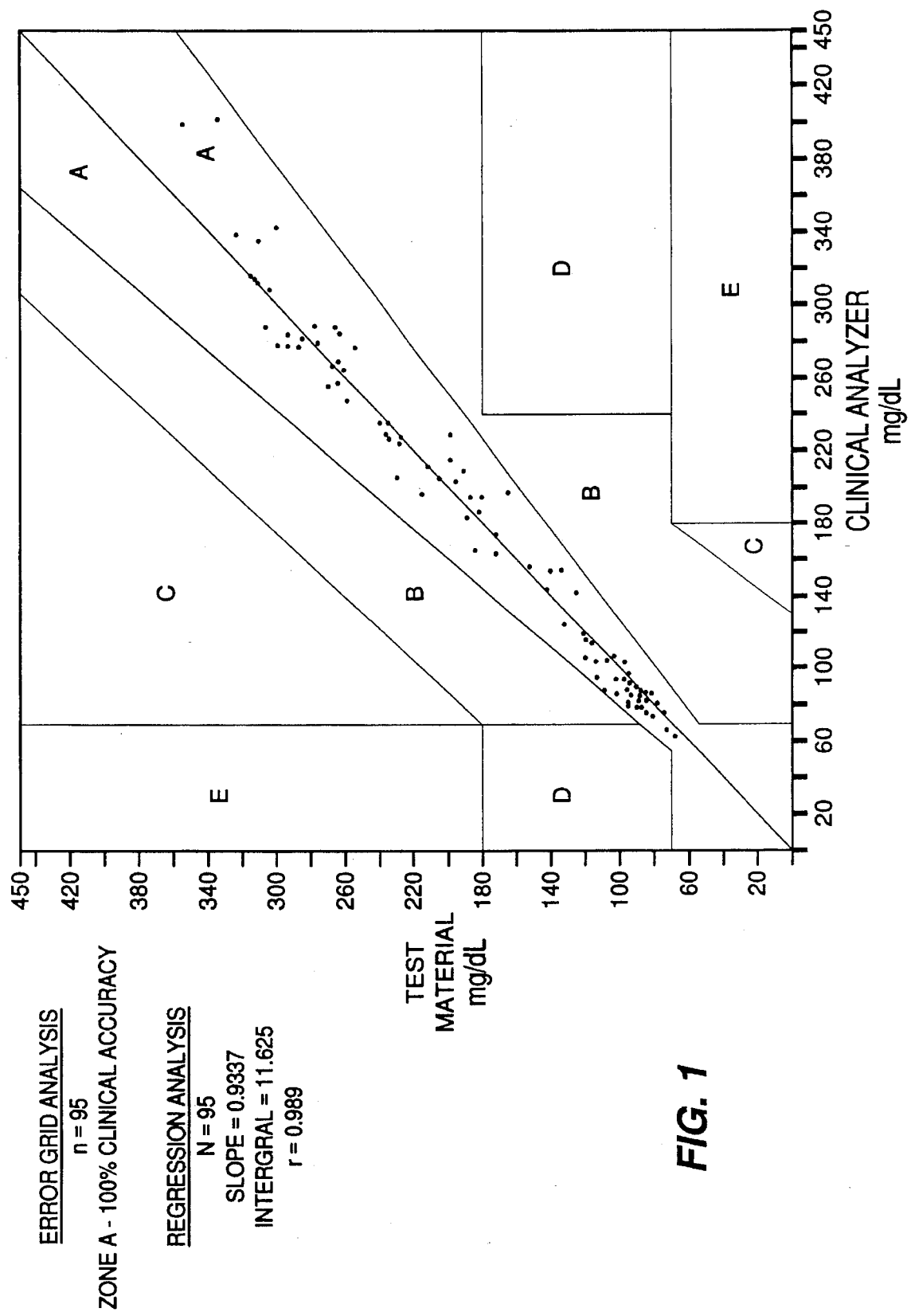

TEST STRIP FOR BLOOD GLUCOSE TESTING

BACKGROUND OF THE INVENTION

The present invention relates to the detection of blood analyte levels, and is more particularly directed to a test strip which may be used to determine blood glucose levels.

It is desirable to determine and monitor blood glucose levels of patients with diabetes. Diabetic patients fall into several categories, but in all cases it is desirable to monitor, or have monitored, the blood glucose level on a frequent basis.

Self-monitoring of blood glucose by diabetic patients at home or other non-laboratory settings is increasingly common. Self-monitoring by the patient provides a means for frequent measurement of blood glucose. These measurements are important in a number of diabetic circumstances, including pregnancy, unstable diabetic conditions, propensities toward severe ketosis or hypoglycemia, an unexpected lack of the usual warning symptoms for hypoglycemia, the use of portable insulin infusion devices or multiple daily injections, and other particular circumstances.

With the increasing availability of spectroscopy and spectroscopic devices at inexpensive cost, both general and specific photometric devices have been developed which can identify chemical compounds based on their interaction with a range of electromagnetic radiation, as well as photometers specifically tailored to identify the presence and concentration of a single analyte such as glucose.

As used herein, the term "spectroscopy" refers to the analytical technique of directing incident light at a designated sample, reading the light following its interaction with the sample, and then making a determination of the contents of the sample based upon some measured differences between the incident light and the detected light. Devices for accomplishing such analysis can be referred to as "photometers", "spectrophotometers", or "spectrometers". As used herein, the term "photometer" will refer to such devices.

In the past, such devices were rather large with delicate and complicated light paths, optics capable of generating an entire spectrum of light within a given range (ultraviolet, infrared, microwave, etc.), hardware for holding liquid samples and for directing the desired frequencies of light through the samples, and often a reference "blank" which carried a solvent identical to that used in the sample in order to provide appropriate calibration. The complexity of such devices prevented their use for practical self-monitoring by individual diabetic patients.

The most common means of self monitoring currently in use incorporate a "test strip." Test strips used in the prior art typically have a substrate which carries some chemicals which change color in the presence of an analyte such as glucose. The degree of color change is dependent on the analyte level. The user can compare the resulting color which develops with a standard chart and thereby measure and monitor their blood glucose level.

In use, the patient adds a sample of blood to the test strip, waits a predetermined amount of time during which the strip changes color, and then compares the color of the strip to the standard color chart at the end of the time period. Given the difference in color perception between individuals, the characteristic poor vision of some diabetics, the difficulty with properly measuring the sample of blood, the problems in precisely timing the reaction, the continuously changing color of the test strip, variations in the test strip chemistry from batch to batch, and other inherent inaccuracies of such testing methods, the results are often unreliable. Accordingly, the development of simple photometers with which lay persons can read a digital output of the glucose level has improved home monitoring of glucose levels by diabetics.

The development of "microelectronic" technology has made photometers available to the general public at affordable prices, and where the sole purpose of the device is to determine the presence and amount of a single known analyte such as glucose, the design can be simplified. Accordingly, a number of smaller instruments are readily available as self-monitoring devices with which lay persons can attempt to diagnose their own blood chemistry.

As used in the prior art, whole blood is placed on the reagent portion of the test strip. The whole blood is reacted with enzymes, such as glucose oxidase and horseradish peroxidase, with hydrogen peroxide resulting from the reaction. Hydrogen peroxide oxidizes a chromophore, which yields a color on the test strip in proportion to the glucose concentration present in the blood. In typical use, after the reaction occurs, the test strip is placed into a commercially available photometer, which measures the color formed by the reaction. The photometer then typically translates the color into a digital display which gives a value for the level of the glucose present in the blood, normally in mg/dL.

The color change on most test strips is from a white or beige color to shades of blues and greens. Either by visual determination, or by use of the photometer, the degree of change gives an indication of the amount of analyte, such as glucose, which is present. Since the determination of blood glucose level by visual comparison of the reacted test strip with a color chart requires interpretation by the user, there are inherent deficiencies in the accuracy.

While photometers tend to be more accurate, the test strips which have used color changes to blue-green are not always clinically accurate. "Clinically accurate" is defined as glucose reading levels which yield values falling within a range which lead to clinically correct treatment decisions (Evaluating Clinical Accuracy for Self Monitoring of Blood Glucose, Clarke et al., Diabetes Care, Vol 10, No. 5, pp 622–627, 1987). In one test, the One Touch photometer was within 15% of the correct glucose level only 86% of the time, and the Accucheck III was within 15% of the correct level only 76% of the time. The American Diabetes Association has stated that self monitoring of blood glucose should, at all times, be within 15% of the results of the reference method.

SUMMARY OF THE INVENTION,

The present invention provides a test strip which may be used with a photometer to provide readings which are within 15% of correct blood glucose level 95% of the time, and within 20% of correct blood glucose level approaching 100% of the time, if the test strip and photometer are used correctly. The reacted test strip within the photometer provides a reading, which, when used correctly, approaches 100% clinical accuracy as that term is defined. The test strip is used in the same manner as test strips which are known in the art and which are used with photometers known in the art.

The present invention is comprised of a substrate, which may be a plastic strip of the proper width for insertion into the photometer. A portion of the plastic strip is coated with a reagent composition, which is comprised of one or more enzymes, one or more chromophores, a copolymer, a resin emulsion and a filler. If this formulation is used, the chromophores will yield blue-green colors, with the exact color determined by the level of glucose present in the blood sample.

The present invention further comprises a color dye additive to produce red tones. In the preferred embodiment, Food and Dye Color Red #40, Food and Dye Color Red #3 and Food and Dye Color Blue #1 are added to the reagent composition.

Further, in the preferred embodiment, a copolymer is added which will yield a polymeric matrix for the reagent which will bond the reagent to the substrate. The preferred copolymer achieves complete coalescence and yields a smooth surface when the reagent dries on the substrate.

The use of the dye color additives causes the reagent strip to change to varying shades of blue, depending on the level of glucose which is present in the blood sample. The dye color yields a test strip which may be read by a photometer which is specifically designed to "read" light reflected within the wave length of the colors produced by the reaction of the glucose with the reagent. The use of the red dye color additive yields blue tones, as opposed to the blue-green tones of the prior art, producing a test strip which may be read by a photometer, and which has a clinical accuracy which approaches 100%. The use of the copolymer produces a smooth surface on the reagent, and aids in the achievement of very accurate readings.

DESCRIPTION OF THE DRAWINGS

FIG 1 is a graph showing multiple readings taken from the digital output of a photometer after the photometer read the test strip of the present invention. Area A of the graph demonstrates readings which are within 15% of the correct blood glucose level, with the line which bisects area A indicating a 100% accurate reading.

DETAILED DESCRIPTION OF THE PREFERRED EMBODIMENT

One or more enzymes are combined with one or more chromophores. The enzymes may be glucose oxidase and peroxidase The chromophore may be 3, 3', 5, 5' tetramethyl benzidine. The enzymes and chromophores, the "active ingredients", are suspended in a polymeric matrix of polymer resin emulsion, vinyl acetate ethylene copolymer, and polyvinyl acetate. Boric acid may be added. Hydroxypropyl methylcellulose may be added as a filler.

The polymeric matrix in which the active ingredients are suspended are applied to a substrate. The substrate could be various materials which are capable of formation into strips. The strips must be of a sufficient width and thickness to allow application of the polymeric matrix to achieve reaction and subsequent photometric reading by the photometer. The width of the strip and thickness is, therefore, determined by the dimensions of the slot of the photometer into which the strip is inserted. The substrate may be plastic. The substrate may be any material onto which the polymeric matrix may be applied and to which the polymer will adhere, and which may be formed into suitable dimensions for use with the photometer.

The polymeric matrix in which the reagent composition is suspended is prepared to form a viscous liquid. The viscous liquid may be applied by a peristaltic pump to the substrate. Other means of coating substrates with liquid polymers could be used. A leveling blade may be used to form the polymeric matrix to the desired thickness on the substrate. The test strip is then fed through a hot air drying tunnel. The test strip may be cut to the desired width and length after the polymer is applied and dried.

The resin emulsion is a polymer. A formulated resin emulsion sold by National Starch and Chemical Company may be used. The enzyme solution is horseradish peroxidase and glucose oxidase. The enzyme solution may comprise 9682 units of horseradish peroxidase and 5779 units of glucose oxidase in one ml of phosphate buffered solution. A chromophore solution may be $3,3^1,5,5^1$ tetramethyl benzidine, in a solution of 10% gantrez and dioctyl sulfosuccinate. The polymeric matrix may comprise a vinyl acetate ethylene copolymer, such as AirFlex 465 PEV produced by Air Products and Chemicals, Inc. A filler may be used, which may comprise 5% hydroxypropyl methylcellulose, such as Methocel E 50LV Premium Grade of Dow Chemical, Inc. The sodium cholate, polyvinyl acetate, and boric acid may be placed into solution in water.

Dye color additives are combined to achieve the desired colors. The preferred dye color additives are FD&C Red #40, FD&C Red #3 and FD&C Blue #1. The dyes are placed in solution. An example formulation of the dye color additive is:

|  | % Weight |
| --- | --- |
| Water | 91.24 |
| Propylene glycol | 6.00 |
| Propyl paraben | 0.09 |
| FD&C Red #40 | 2.42 |
| FD&C Red #3 | 0.22 |
| FD&C Blue #1 | 0.03 |
|  | 100% |

An example formulation of the reagent which is applied to the substrate to produce the test strip is as follows (shown in percentages by weight):

|  | % Weight |
| --- | --- |
| Resin emulsion | 37.8–39.4 |
| Enzyme solution | 1.0–1.1 |
| $3,3^1,5,5^1$ tetramethyl benzidine | 3.2–3.5 |
| 20% Sodium Cholate | 3.4–3.7 |
| 10% Polyvinyl Acetate | 11.4–12.4 |
| Vinyl Acetate - Ethylene Copolymer | 10.3–11.4 |
| 5% Hydroxypropyl Methylcellulose | 27.8–30.1 |
| 5% Boric Acid | 1.2–1.3 |
| Dye color additive | 0.1 |
|  | 100% |

A preferred formulation for the reagent is as follows:

|  | % Weight |
| --- | --- |
| Resin emulsion | 38.6 |
| Enzyme solution | 1.0 |
| $3,3^1,5,5^1$ tetramethyl benzidine | 3.5 |
| 20% Sodium Cholate | 3.7 |
| 10% Polyvinyl Acetate | 11.9 |
| Vinyl Acetate - Ethylene Copolymer | 10.9 |
| 5% Hydroxypropyl Methylcellulose | 29.1 |
| 5% Boric Acid | 1.2 |
| Dye color additive | 0.1 |
|  | 100% |

In use, a drop of blood is placed on the polymer coated reagent area of the test strip. The start button is pressed on the photometer. Excess blood is wiped from the strip with an appropriate material, and the portion of the strip where the blood and reagent are present is inserted into the slot in the photometer. The photometer will display the blood glucose level by means of a digital display on the photometer.

A copolymer which achieves complete coalescence of the surface particle structure is preferred for use in the reagent. This complete coalescence produces a smooth surface having a fine particle structure which reflects light in the photometer to allow the photometer to achieve the desired level of accuracy, especially when the dye color additive is used to allow reflectance in the red color frequencies of the spectrum.

The preferred copolymer is an emulsion prior to mixing with the active reagents and which has a high solids content of not less than 66%, and relatively low viscosity when compared to other vinyl acetate ethlyene copolymers. Airflex 465 DEV manufactured by Air Products and Chemicals, Inc. or a vinyl acetate ethylene copolymer having comparable properties may be used.

FIG. 1 is a graph showing multiple readings taken from the digital output of a photometer plotted on the graph, after the photometer reads multiple test strips of the present invention which have reacted with whole blood. Area A of the graph demonstrates readings which are within 15% of the correct blood glucose level, with the line which bisects area A indicating a 100% accurate reading. All readings taken from the photometer and plotted on the graph are within area A.

What is claimed:

1. A test strip for use with a photometer for determining blood glucose levels, comprising a substrate having a red colored reagent thereon, wherein the reagent comprises at least one enzyme, at least one chromophore, and at least one red dye additive.

2. A test strip for use with a photometer for determining blood glucose levels as described in claim 1, wherein said chromophore is tetramethyl benzidine.

3. A test strip for use with a photometer for determining blood glucose levels as described in claim 1, wherein said red dye additive comprises Food Dye and Coloring Red Number 40, Food Dye and Coloring Red Number 3, and Food Dye and Coloring Blue Number 1.

4. A test strip for use with a photometer for determining blood glucose levels as described in claim 3, wherein said chromophore is tetramethyl benzidine.

5. A test strip for use with a photometer for determining blood glucose levels as described in claim 1, wherein said reagent further comprises a copolymer.

6. A test strip for use with a photometer for determining blood glucose levels as described in claim 5, wherein said chromophore is tetramethyl benzidine.

7. A test strip for use with a photometer for determining blood glucose levels as described in claim 5, wherein said red dye additive comprises Food Dye and Coloring Red Number 40, Food Dye and Coloring Red Number 3, and Food Dye and Coloring Blue Number 1.

8. A test strip for use with a photometer for determining blood glucose levels as described in claim 7, wherein said chromophore is tetramethyl benzidine.

9. A test strip for use with a photometer for determining blood glucose levels as described in claim 5, wherein said copolymer is a vinyl acetate ethylene copolymer.

10. A test strip for use with a photometer for determining blood glucose levels as described in claim 9, wherein said copolymer achieves complete coalescence.

11. A test strip for use with a photometer for determining blood glucose levels as described in claim 9, wherein said red dye additive comprises Food Dye and Coloring Red Number 40, Food Dye and Coloring Red Number 3, and Food Dye and Coloring Blue Number 1.

12. A test strip for use with a photometer for determining blood glucose levels as described in claim 10, wherein said red dye additive comprises Food Dye and Coloring Red Number 40, Food Dye and Coloring Red Number 3, and Food Dye and Coloring Blue Number 1.

13. A test strip for use with a photometer for determining blood glucose levels comprising a substrate having a red colored reagent coated thereon, wherein the reagent is a polymeric matrix comprising polymer resin, vinyl acetate ethylene copolymer, at least one enzyme, at least one chromophore, and at least one red dye additive.

14. A test strip for use with a photometer for determining blood glucose levels as described in claim 13, wherein said chromophore is tetramethyl benzidine.

15. A test strip for use with a photometer for determining blood glucose levels as described in claim 13, wherein said red dye additive comprises Food Dye and Coloring Red Number 40, Food Dye and Coloring Red Number 3, and Food Dye and Coloring Blue Number 1.

16. A test strip for use with a photometer for determining blood glucose levels as described in claim 15, wherein said red dye additive further comprises water, propylene glycol, and propyl paraben.

17. A test strip for use with a photometer for determining blood glucose levels as described in claim 15, wherein said chromophore is tetramethyl benzidine.

18. A test strip for use with a photometer for determining blood glucose levels as described in claim 15, wherein said copolymer achieves complete coalescence.

19. A test strip for use with a photometer for determining blood glucose levels as described in claim 18, wherein said red dye additive further comprises water, propylene glycol, and propyl paraben.

* * * * *